United States Patent
Woods et al.

(10) Patent No.: US 11,957,467 B2
(45) Date of Patent: Apr. 16, 2024

(54) NEURAL STIMULATION THROUGH AUDIO WITH DYNAMIC MODULATION CHARACTERISTICS

(71) Applicant: BrainFM, Inc., Brooklyn, NY (US)

(72) Inventors: Kevin J. P. Woods, Brooklyn, NY (US); Daniel Clark, Brooklyn, NY (US)

(73) Assignee: BrainFM, Inc., Brooklyn, NY (US)

( * ) Notice: Subject to any disclaimer, the term of this patent is extended or adjusted under 35 U.S.C. 154(b) by 0 days.

(21) Appl. No.: 17/366,896

(22) Filed: Jul. 2, 2021

(65) Prior Publication Data

US 2023/0000410 A1 Jan. 5, 2023

(51) Int. Cl.
  *A61B 5/16* (2006.01)
  *A61B 5/00* (2006.01)
  *G06F 3/01* (2006.01)
  *H04R 5/04* (2006.01)

(52) U.S. Cl.
  CPC ............ *A61B 5/165* (2013.01); *A61B 5/4064* (2013.01); *G06F 3/015* (2013.01); *H04R 5/04* (2013.01); *H04R 2410/01* (2013.01)

(58) Field of Classification Search
  None
  See application file for complete search history.

(56) References Cited

U.S. PATENT DOCUMENTS

| | | |
|---|---|---|
| 3,712,292 A | 1/1973 | Zentmeyer |
| 4,141,344 A | 2/1979 | Barbara |
| 4,191,175 A | 3/1980 | Nagle |
| 4,227,516 A | 10/1980 | Meland et al. |
| 4,315,502 A | 2/1982 | Gorges |
| 4,777,529 A | 10/1988 | Schultz et al. |
| 5,135,468 A | 8/1992 | Meissner |
| 5,213,562 A | 5/1993 | Monroe |
| 5,289,438 A | 2/1994 | Gall |

(Continued)

OTHER PUBLICATIONS

Greenburg et al. "The Modulation Spectrogram: In Pursuit of an Invariant Representation of Speech", Presented at ICASSP-97, vol. 3, pp. 1647-1650.

(Continued)

*Primary Examiner* — Alex M Valvis
*Assistant Examiner* — Aurelie H Tu
(74) *Attorney, Agent, or Firm* — Akerman LLP

(57) ABSTRACT

Techniques (methods and devices) for neural stimulation through audio with dynamic modulation characteristics are disclosed. The techniques include receiving a mapping of sensor-input values and modulation-characteristic values, wherein each sensor-input value corresponds to a respective modulation-characteristic value; receiving an audio element from an audio source, wherein the audio element comprises at least one audio parameter; identifying an audio-parameter value of the audio parameter; receiving a sensor-input value from a sensor; determining a sensor-input value based on the sensor-input value; selecting from the mapping of sensor-input values and modulation-characteristic values, a modulation-characteristic value that corresponds to the sensor-input value; generating an audio output based on the audio-parameter value and the modulation-characteristic value; and playing the audio output.

20 Claims, 6 Drawing Sheets

(56) References Cited

U.S. PATENT DOCUMENTS

| | | | |
|---|---|---|---|
| 5,586,967 | A | 12/1996 | Davis |
| 7,674,224 | B2 | 3/2010 | Hewett |
| 2001/0049480 | A1 | 12/2001 | John et al. |
| 2003/0089218 | A1 | 5/2003 | Gang |
| 2007/0084473 | A1 | 4/2007 | Hewett |
| 2007/0291958 | A1 | 12/2007 | Jehan |
| 2008/0097633 | A1 | 4/2008 | Jochelson |
| 2010/0005686 | A1 | 1/2010 | Russell |
| 2010/0056854 | A1 | 3/2010 | Chang |
| 2010/0188580 | A1 | 7/2010 | Paschalakis et al. |
| 2011/0169603 | A1 | 7/2011 | Fithian |
| 2012/0251989 | A1 | 10/2012 | Wemore |
| 2013/0046546 | A1 | 2/2013 | Uhle et al. |
| 2013/0216055 | A1 | 8/2013 | Wanca |
| 2014/0223462 | A1* | 8/2014 | Aimone ............ H04N 21/4307 725/10 |
| 2014/0330848 | A1 | 11/2014 | Chen |
| 2015/0016613 | A1 | 1/2015 | Atwater et al. |
| 2015/0199010 | A1* | 7/2015 | Coleman ................ A61B 5/369 345/156 |
| 2015/0297109 | A1* | 10/2015 | Garten .................. A61B 5/375 600/544 |
| 2015/0351655 | A1* | 12/2015 | Coleman ................ G16H 50/20 600/301 |
| 2015/0356876 | A1 | 12/2015 | Wang |
| 2016/0143554 | A1* | 5/2016 | Lim .................... A61B 5/6803 600/386 |
| 2016/0372095 | A1 | 12/2016 | Lyske |
| 2017/0024615 | A1 | 1/2017 | Allen et al. |
| 2017/0043236 | A1 | 2/2017 | Li |
| 2017/0124074 | A1 | 5/2017 | Cama |
| 2017/0339484 | A1* | 11/2017 | Kim ........................ A61B 5/165 |
| 2017/0371961 | A1 | 12/2017 | Douglas |
| 2018/0315452 | A1 | 11/2018 | Shi et al. |
| 2020/0074982 | A1 | 3/2020 | McCallum |
| 2020/0213790 | A1 | 7/2020 | Osborne |
| 2020/0275875 | A1* | 9/2020 | Johnstone .............. A61B 5/165 |

OTHER PUBLICATIONS

Moritz, et al. "An Auditory Inspired Amplitude Modulation Filter Bank for Robust Feature Extraction in Automatic Speech Recognition", IEEE/ACM Transactions on Audio, Speech, and Language Processing, vol. 23, No. 11, Nov. 2015.

Singh et al. Modulation Spectra of Natural Sounds and Ethological Theories of Auditory Processing, J. Acoust. Soc. Am, 114 (6), Pt. 1, pp. 3394-3411, Dec. 2003.

International Search Report issued in International Applicatio No. PCT/US2020/017788 dated Apr. 29, 2020, 2 pages.

Written Opinion issued in International Applicatio No. PCT/US2020/017788 dated Apr. 29, 2020, 5 pages.

Non-Final Office Action issued in U.S. Appl. No. 17/505,453 dated May 4, 2023 (32 pages).

* cited by examiner

NEURAL STIMULATION THROUGH AUDIO WITH DYNAMIC MODULATION CHARACTERISTICS

RELATED APPLICATIONS

This application is related to U.S. Pat. Nos. 7,674,224, 10,653,857 and U.S. Patent Publication No. 2020/0265827, all of which are incorporated herein by reference.

FIELD

The present disclosure relates to neural stimulation, particularly, noninvasive neural stimulation using audio.

BACKGROUND

For decades, neuroscientists have observed wave-like activity in the brain called neural oscillations. Various aspects of these oscillations have been related to mental states including attention, relaxation, and sleep. The ability to effectively induce and modify such mental states by noninvasive brain stimulation is desirable.

OVERVIEW

Certain embodiments disclosed herein enable the modification of modulation characteristics of an audio source to effectively induce and modify brain stimuli to induce desirable mental states.

Some example embodiments include: receiving, by a processing device, a mapping of sensor-input values and modulation-characteristic values, wherein each sensor-input value maps to a respective modulation-characteristic value; receiving, by the processing device, an audio element from an audio source, wherein the audio element comprises at least one audio parameter; identifying, by the processing device, an audio-parameter value of the audio parameter; receiving, by the processing device, a sensor-input value from a sensor; determining, by the processing device, from the mapping of sensor-input values and modulation-characteristic values, a modulation-characteristic value that corresponds to the sensor-input value; generating, by the processing device, an audio output based on the audio-parameter value and the modulation-characteristic value; and playing, by the processing device, the audio output. In some cases, user-associated data can be received by the processing device in addition to the sensor-input value and the determining of the modulation-characteristic value can be based on either or both of sensor-input value or the user-associated data.

In various example embodiments, the modulation-characteristic value may correspond to a modulation characteristic comprising modulation rate, phase, depth, or waveform shape. In example embodiments, the audio source may comprise at least one of an audio signal, digital music file, musical instrument, or environmental sounds. In example embodiments, the audio parameter may comprise at least one of tempo, root mean square energy, loudness, event density, spectrum, temporal envelope, cepstrum, chromagram, flux, autocorrelation, amplitude modulation spectrum, spectral modulation spectrum, attack and decay, roughness, harmonicity, or sparseness.

In some example embodiments, the sensor-input value may correspond to a sensor type comprising at least one of an inertial sensor (e.g., accelerometer, gyrometer, and magnetometer), a microphone, a camera, or a physiological sensor. In example embodiments the physiological sensor may comprise one or more sensors that measure heart rate, blood pressure, body temperature, EEG, MEG, Near infrared (fNIRS), or bodily fluid. In some example embodiments, the receiving of the sensor-input may comprise receiving background noise from the microphone, inertial data from an accelerometer, images from a camera, etc. In some example embodiments, the sensor-input value may correspond to a measure of user activity on a device such as, for example, a smart phone, computer, tablet, or the like. In some example embodiments, the measure of user activity may be the number of, type of, or time applications are being interacted with on the device.

In some example embodiments, generating the mapping of sensor-input values and modulation-characteristic values can be based on a type of sensor and/or a modulation characteristic. In some example embodiments, the mapping of sensor-input values and modulation-characteristic values may be stored in a data table. In some embodiments, the audio output can be transmitted from the processing device to an external device for playback.

In some embodiments, a processing device comprising a processor and associated memory is disclosed. The processor can be configured to: receive, a mapping of sensor-input values and modulation-characteristic values, wherein each sensor-input value corresponds to a respective modulation-characteristic value, receive an audio element from an audio source, wherein the audio element comprises at least one audio parameter, identify an audio-parameter value of the audio parameter, receive a sensor-input value from a sensor, determine from the mapping of sensor-input values and modulation-characteristic values, a modulation-characteristic value that corresponds to the sensor-input value, generate an audio output based on the audio-parameter value and the modulation-characteristic value, and play the audio output.

BRIEF DESCRIPTION OF DRAWINGS

Other objects and advantages of the present disclosure will become apparent to those skilled in the art upon reading the following detailed description of exemplary embodiments and appended claims, in conjunction with the accompanying drawings, in which like reference numerals have been used to designate like elements, and in which:

The figures are for purposes of illustrating example embodiments, but it is understood that the inventions are not limited to the arrangements and instrumentality shown in the drawings. In the figures, identical reference numbers identify at least generally similar elements.

DESCRIPTION

The present disclosure describes systems, methods, apparatuses and computer executable media configured to vary the modulation characteristics of audio to affect neural activity. Modulation characteristics may include depth of modulation at a certain rate, the rate itself, modulation depth across all rates (i.e., the modulation spectrum), phase at a rate, among others. These modulation characteristics may be from the broadband signal or in sub-bands (e.g., frequency regions, such as bass vs. treble). Audio/audio element, as used herein, can refer to a single audio element (e.g. a single digital file), an audio feed (either analog or digital) from a received signal, or a live recording.

In various exemplary embodiments described herein, the presently disclosed techniques can be effective when audio stimulation is provided by predetermined frequencies, which are associated with known portions of the cochlea of the human ear and may be referenced in terms of the cochlea, or in terms of absolute frequency. Furthermore, the presently disclosed techniques may provide for a selection of modulation characteristics configured to target different patterns of brain activity. These aspects are subsequently described in detail.

In various exemplary embodiments described herein, audio can be modulated according to a stimulation protocol to affect patterns of neural activity in the brain to affect behavior and/or sentiment. Modulation can be added to audio (e.g., mixed) which can in turn be stored and retrieved for playback at a later time. Modulation can be added (e.g., mixed) to audio for immediate (e.g., real-time) playback. Modulated audio playback may be facilitated from a playback device (e.g., smart speaker, headphone, portable device, computer, etc.) and may be single or multi-channel audio. Users may facilitate the playback of the modulated audio through, for example, an interface on a processing device (e.g., smartphone, computer, etc.). These aspects are subsequently described in detail.

Figure 1A:
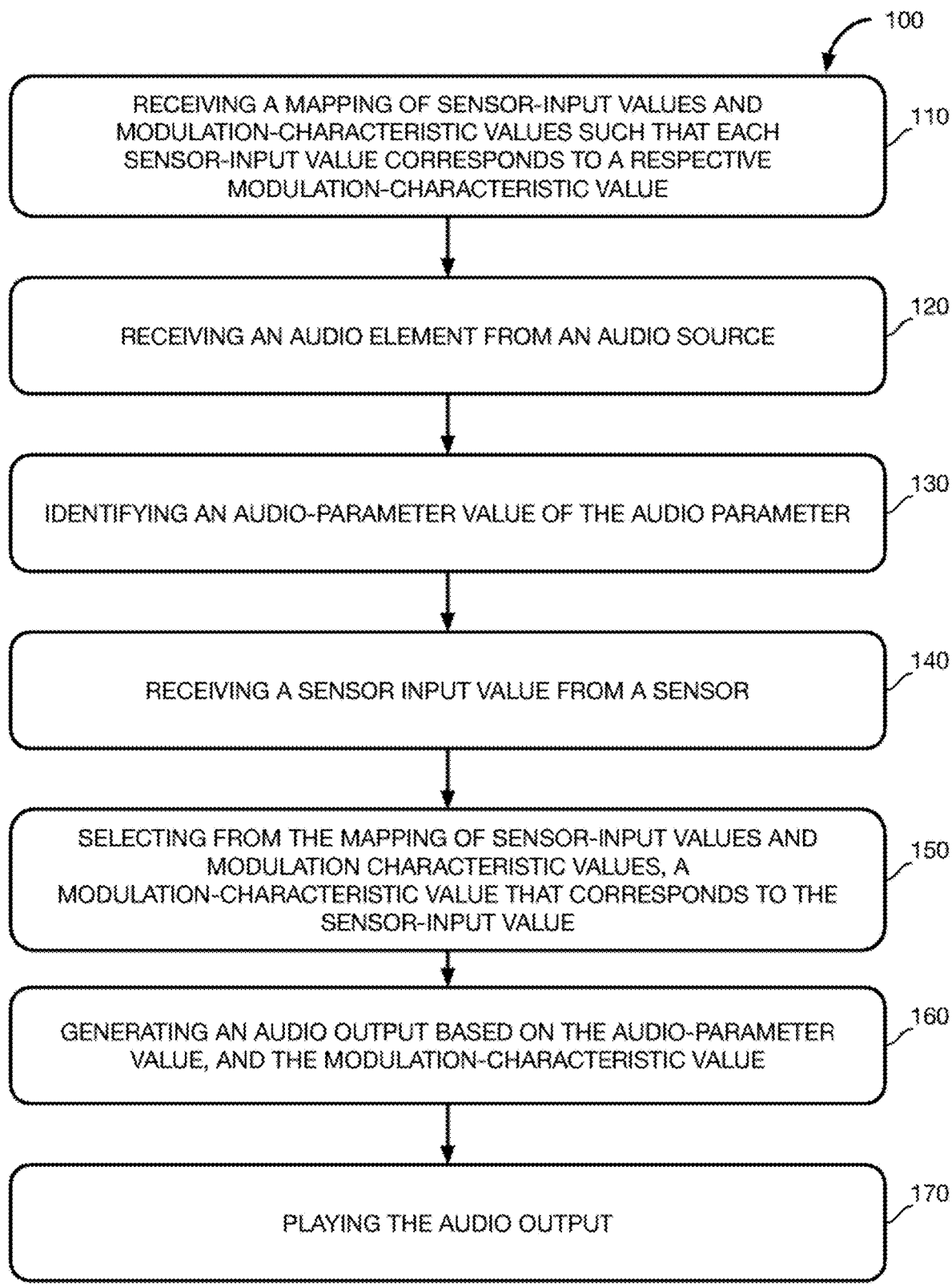
FIG. 1A is a flowchart of a method according to an example embodiment of the present disclosure.

FIG. 1A illustrates an example method 100 performed by a processing device (e.g. smartphone, computer, etc.) according to an example embodiment of the present disclosure. The method 100 may include one or more operations, functions, or actions as illustrated in one or more of blocks 110-180. Although the blocks are illustrated in sequential order, these blocks may also be performed in parallel, and/or in a different order than the order disclosed and described herein. Also, the various blocks may be combined into fewer blocks, divided into additional blocks, and/or removed based upon a desired implementation.

Method 100 can include a block 110 of receiving a mapping of sensor-input values and modulation-characteristic values such that each sensor-input value corresponds to a respective modulation-characteristic value. The mapping can be based on a predetermined or real-time computed map. Non-limiting examples of mappings include: a phone with an accelerometer that detects movement and reports an estimate of user productivity and mapping this productivity estimate to modulation depth such that the level of modulation increases if estimated productivity slows down; a mobile device with an accelerometer detects movements and reports user started a run (e.g. by using the CMMotionActivity object of Apple's iOS Core ML framework) which maps to a slight shift in the phase of modulation relative to the phase of the underlying music, at an increased run speed; and a microphone that detects background noise in a particular frequency band (e.g., HVAC noise concentrated in bass frequencies) which maps to increased modulation depth in that sub-band, for masking. In an example embodiment, the mapping can be based on a type of sensor and/or a modulation characteristic. Other examples exist. The mapping can be stored in a data table as shown in the example below in table 1 or stored as a function, such as, for example, $f(x)=x^2$ where x is the sensor-input value and f(x) is the modulation characteristic value.

TABLE 1

| Sensor input values (High-frequency Heart Rate Variability (HF-HRV), ms) | Modulation-characteristic values (Desired final mixdown modulation depth, % normalized re.max) |
|---|---|
| 20 | 90 |
| 30 | 80 |
| 40 | 70 |
| 50 | 60 |
| 60 | 50 |
| 70 | 40 |
| 80 | 30 |
| 90 | 25 |
| 100 | 22 |
| 110 | 19 |
| 120 | 17 |
| 130 | 15 |
| 140 | 13 |
| 150 | 12 |
| 160 | 11 |
| 170 | 10 |
| 180 | 10 |
| 190 | 10 |
| 200 | 10 |

In an example embodiment, modulation rate, phase, depth, and waveform can be four non-exclusive modulation characteristics. Modulation rate can be the speed of the cyclic change in energy, and can be defined, for example, in hertz. Phase is the particular point in the full cycle of modulation, and can be measured, for example, as an angle in degrees or radians. Depth can indicate the degree of amplitude fluctuation in the audio signal. In amplitude modulation, depth can be expressed as a linear percent reduction in signal power or waveform envelope from peak-to-trough, or as the amount of energy at a given modulation rate. Waveform may express the shape of the modulation cycle, such as a sine wave, a triangle wave or some other custom wave. These modulation characteristics can be extracted from the broadband signal or from sub-bands after filtering in the audio-frequency domain (e.g., bass vs. treble), by taking measures of the signal power over time or by calculating a waveform envelope (e.g., the Hilbert envelope).

According to example embodiments, a stimulation protocol may provide one or more of a modulation rate, phase, depth and/or waveform for the modulation to be applied to audio data that can be used to induce neural stimulation or entrainment. Neural stimulation via such a stimulation protocol may be used in conjunction with a cochlear profile to induce different modes of stimulation in a user's brain.

At block 120, an audio element is received at the processing device from an audio source. The audio element can be, for example, a digital audio file retrieved by the processing device from local storage on the processing device or from remote storage on a connected device. In an example, the digital audio file is streamed to the processing device from a connected device such as a cloud server for an online music service (e.g., Spotify, Apple Music, etc.). In another example, the audio element may be received by the processing device from an audio input such as a microphone. The audio source can include, for example, an audio signal, digital music file, musical instrument, or environmental sounds. The audio element can be in the form of one or more audio elements read from a storage medium, such as, for example, an MP3 or WAV file, received as an analog signal, generated by a synthesizer or other signal generator, or recorded by one or more microphones or instrument transducers, etc. The audio elements may be embodied as a digital music file (.mp3, .wav, .flac, among others) representing sound pressure values, but could also be a data file read by other software which contains parameters or instructions for sound synthesis, rather than a representation of sound itself. The audio elements may be individual instruments in a musical composition, groups of instruments (bussed outputs), but could also be engineered objects such as frequency sub-bands (e.g., bass frequencies vs treble frequencies). The content of the audio elements may include music, but also non music such as environmental sounds (wind, water, cafe noise, and so on), or any sound signal such as a microphone input.

In an example embodiment, to achieve better brain stimulation, a wide spectrum of audio elements may be used. Accordingly, the audio elements may be selected such that they have a wide (i.e., broadband) spectral audio profile—in other words, the audio elements can be selected such that they include many frequency components. For example, the audio elements may be selected from music composed from many instruments with timbre that produces overtones across the entire range of human hearing (e.g., 20-20 kHz).

At block 130, an audio-parameter value of the audio parameter can be identified. The audio element may be characterized by one or more audio parameters. For example, audio parameters may include tempo; RMS (root mean square energy in signal); loudness (based on perceptual transform); event density (complexity/business); spectrum/spectral envelope/brightness; temporal envelope ('outline' of signal); cepstrum (spectrum of spectrum); chromagram (what pitches dominate); flux (change over time); autocorrelation (self-similarity as a function of lag); amplitude modulation spectrum (how is energy distributed over temporal modulation rates); spectral modulation spectrum (how is energy distributed over spectral modulation rates); attack and decay (rise/fall time of audio events); roughness (more spectral peaks close together is rougher; beating in the ear); harmonicity/inharmonicity (related to roughness but calculated differently); and/or zero crossings (sparseness). One or more of these may be performed, for example, as multi-timescale analysis of features (different window lengths); analysis of features over time (segment-by-segment); broadband or within frequency sub-bands (i.e. after filtering); and/or second order relationships (e.g., flux of cepstrum, autocorrelation of flux).

At block 140, a sensor-input value can be received from a sensor. The sensor can be on the processing device or it can be on an external device and data from the sensor can be transferred to the processing device. In one example, the sensor on a processing device, such as an accelerometer on a mobile phone, can be used to determine how often the phone is moved and can be a proxy for productivity. In another example, the sensor on an activity tracker (external device), for e.g. an Oura ring or Apple watch, can be used to detect if the user is awake or not, how much they are moving, etc.

In some embodiments, the sensors can be occasional-use sensors responsive to a user associated with the sensor. For example, a user's brain response to modulation depth can be measured via EEG during an onboarding procedure which may be done per use or at intervals such as once per week or month. In other embodiments, the sensors can be responsive to the user's environment. For example, characterizing the acoustic qualities of the playback transducer (headphones/speakers) or room using a microphone, electrical measurement, an audiogram, or readout of a device ID. The sensors can measure environmental factors that may be perceived by the user such as color, light level, sound, smell, taste, and/or tactile.

In some embodiments, behavioral/performance testing can be used to calibrate the sensors and/or to compute sensor-input values. For example, a short experiment for each individual to determine which depth is best via performance. Similarly, external information can be used to calibrate the sensors and/or to compute sensor-input values. For example, weather, time of day, elevation of the sun at user location, the user's daily cycle/circadian rhythm, and/or location. Calibration tests, such as measuring calibrating depth of modulation in the music to individual users' sound sensitivity based on a test with tones of increasing loudness can also be used to calibrate the sensors and/or to compute sensor-input values. Of course, each of these techniques can be used in combination or separately. A person of ordinary skill in the art would appreciate that these techniques are merely non-limiting examples, and other similar techniques can also be used for calibration of the sensors.

In example embodiments, the sensor-input value can be obtained from one or more sensors such as, for example, an accelerometer (e.g., phone on table registers typing, proxy for productivity); a galvanic skin response (e.g. skin conductance); video (user-facing: eye tracking, state sensing; outward-facing: environment identification, movement tracking); microphone (user-sensing: track typing as proxy for productivity, other self-produced movement; outward-sensing: environmental noise, masking); heart rate monitor (and heart rate variability); blood pressure monitor; body temperature monitor; EEG; MEG (or alternative magnetic-field-based sensing); near infrared (fnirs); or bodily fluid monitors (e.g., blood or saliva for glucose, cortisol, etc). The one or more sensors may include real-time computation. Non-limiting examples of a real-time sensor computation include: the accelerometer in a phone placed near a keyboard on table registering typing movements as a proxy for productivity; an accelerometer detects movements and reports user started a run (e.g. by using the CMMotionActivity object of Apple's iOS Core ML framework), and microphone detects background noise in a particular frequency band (e.g., HVAC noise concentrated in bass frequencies) and reports higher levels of distracting background noise.

In some embodiments, the received sensor-input value can be sampled at pre-defined time intervals, or upon events, such as the beginning of each track or the beginning of a user session or dynamically on short timescales/real-time: (e.g., monitoring physical activity, interaction with phone/computer, interaction with app, etc.).

In an example embodiment, block 140 can include receiving user-associated data in addition and/or alternatively to the previously described sensor-input value from the sensor (not shown). Alternatively, the block 140 can include receiving only the sensor-input value or user-associated data.

In example embodiments, user-associated data can include self-report data such as a direct report or a survey, e.g., ADHD self-report (ASRS survey or similar), autism self-report (AQ or ASSQ surveys or similar), sensitivity to sound (direct questions), genre preference (proxy for sensitivity tolerance), work habits re. music/noise (proxy for sensitivity tolerance), and/or history with a neuromodulation. Self-report data can include time-varying reports such as selecting one's level of relaxation once per minute, leading to dynamic modulation characteristics over time in response. User-associated data can include behavioral data/ attributes such as user interests, a user's mental state, emotional state, etc. Such information can be obtained from various sources such as the user's social media profile. User-associated data can include factors external to but related to the user such as the weather at the user's location; the time after sunrise or before sunset at the user's location; the user's location; or whether the user is in a building, outdoors, or a stadium.

At block 150, a modulation-characteristic value can be determined. In one example, the modulation-characteristic value is selected from the mapping of sensor-input values and modulation-characteristic values that correspond to the sensor-input value. In another example, the modulation-characteristic value can be calculated by applying the sensor-input values to a mapping function (e.g. $f(x)=x^2$ where x is the sensor-input value and $f(x)$ is the modulation characteristic value).

At block 160, an audio output is generated based on the audio-parameter value and the modulation-characteristic value. The audio output can be generated by varying one or more of a modulation rate, phase, depth and/or waveform in real-time, at intervals, or upon events, such as the beginning of each track or the beginning of a user session. An example goal of the audio output is to achieve a desired modulation characteristic. Details of performing the block 160 are described subsequently in the discussion of responsive modulation determination module in FIG. 2.

At block 170, the modulated audio content is played back via one or more audio drivers of one or more playback devices, such as, for example, a smart speaker, a mobile device, a computer/laptop, an ipad, and the like. In one example, the processing device is the same device as the playback device, and the audio content is played via one or more audio drivers on the processing device itself. In another example, the processing device transmits the audio content (e.g., as a digital file over a data network) to a playback device for playback. In another example, the audio content is played back on the processing device as well as one or more other playback devices.

Figure 1B:
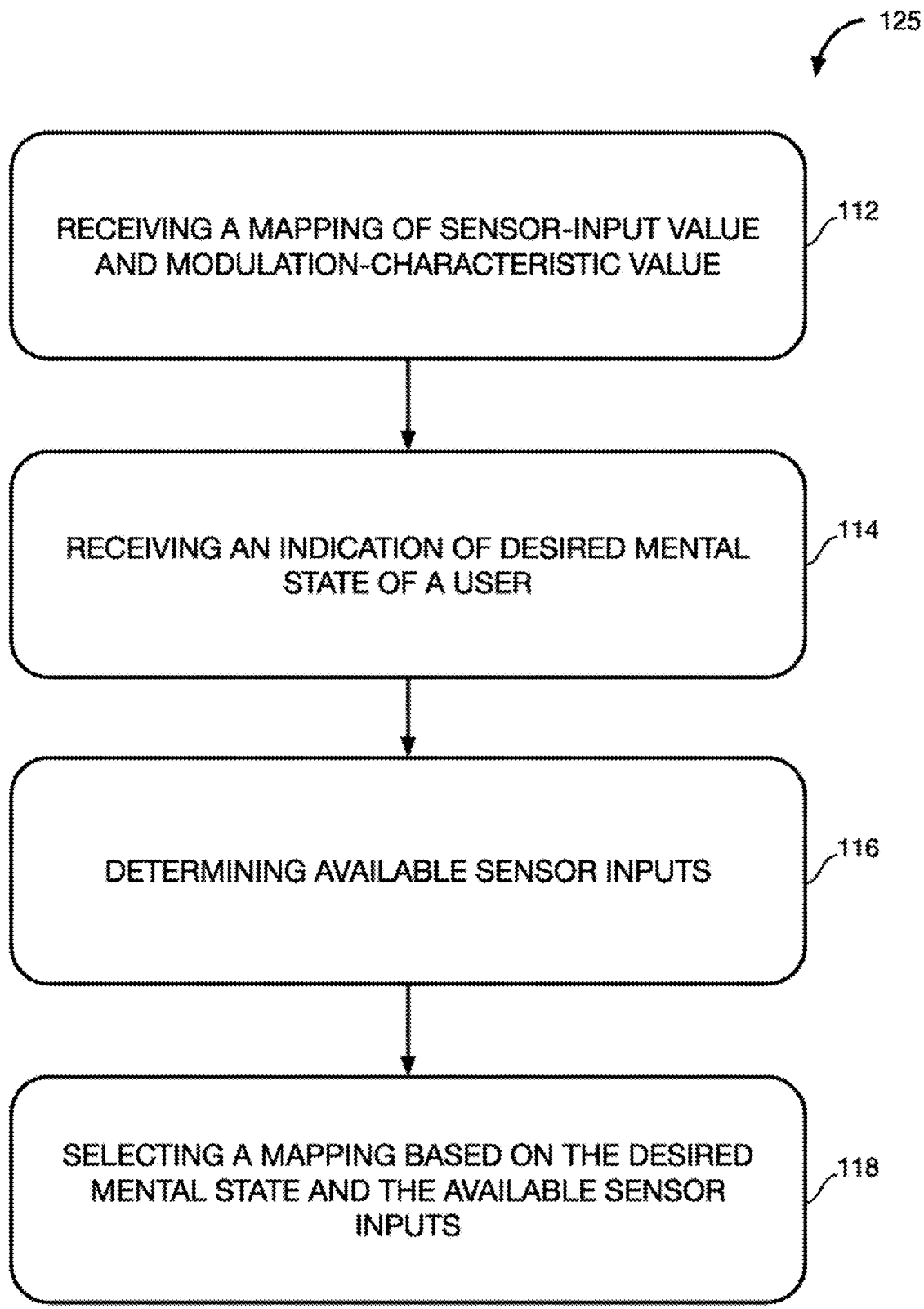
FIG. 1B is a flowchart of a method according to an example embodiment of the present disclosure.

FIG. 1B illustrates an example method 125 performed by a processing device (e.g. smartphone, computer, etc.) according to an example embodiment of the present disclosure. Method 125 depicts generating a mapping of sensor-input values and modulation-characteristic values, as previously discussed in step 110 of FIG. 1A. According to example embodiments of the present disclosure, the method 125 can be performed by the same processing device that performs the method 100. Alternatively, method 125 can be performed by a different processing device (e.g. smartphone, computer, etc.). The method 125 may include one or more operations, functions, or actions as illustrated in one or more of blocks 112, 114, 116, and 118. Although the blocks are illustrated in sequential order, these blocks may also be performed in parallel, and/or in a different order than the order disclosed and described herein. Also, the various blocks may be combined into fewer blocks, divided into additional blocks, and/or removed based upon a desired implementation.

Method 125 can include a block 112, where a mapping of sensor-input value and modulation-characteristic value can be received and/or generated. Aspects of such a mapping have been previously described with respect to step 110 of method 100.

At block 114 an indication of a desired mental state of a user is received. Non-limiting examples of a desired mental state can include focus, relax, sleep, and meditate. Each of these example desired mental states can be further distinguished by a target activity and duration. For example, focus can be distinguished by deep work, creative flow, study and read, and light work; relax can be distinguished by chill, recharge, destress, and unwind; sleep can be distinguished by deep sleep, guided sleep, sleep and wake, and wind down; and meditate can be distinguished by unguided and guided. The duration of the mental state may be specified, for example, by a time duration (e.g., minutes, hours, etc.), or a duration triggered by an event (e.g., waking, etc.). The indication may be received via a user interface on a processing device such as, for example, through an interface on the Brain.fm™ application executing on an iPhone™ or Android™ device. Alternatively and/or additionally, the indication may be received over a network from a different processing device.

At block 116, available sensor inputs can be determined. Available sensor inputs can comprise one or more inputs previously described with respect to block 140 of method 100. At block 118, a mapping is selected based on the desired mental state and the available sensor inputs. In some examples, certain sensor inputs may be more applicable to certain desired mental states. For example, a sleep indication from an Oura ring may be more applicable to the sleep mental state than the focused mental state. In another example, an accelerometer on a mobile device may be more applicable to a focus state than a sleep mental state. A person of ordinary skill in the art would appreciate that the aforementioned examples are non-limiting examples, and many such other examples may exist.

In some examples, multiple sensor inputs may be available, and the processing device may select one (or multiple) sensor inputs to map to a modulation characteristic for a desired mental state. For example, a microphone, accelerometer, application monitor, and Oura ring may be a list of available sensor inputs. In one example, the processing device may determine that the microphone should be used with modulation depth for relax mental state, and the accelerometer should be used with modulation frequency for focus mental state. In another example, the processing device may determine that the accelerometer should be used with modulation frequency for meditation mental state and a sleep indicator from the Oura ring should be used with modulation depth for sleep mental state. In some examples, multiple sensors may be determined to be used with a particular modulation characteristic, and the determination of which sensor(s) to use may be determined dynamically based on the information (or lack of information) available from a sensor.

Figure 2:
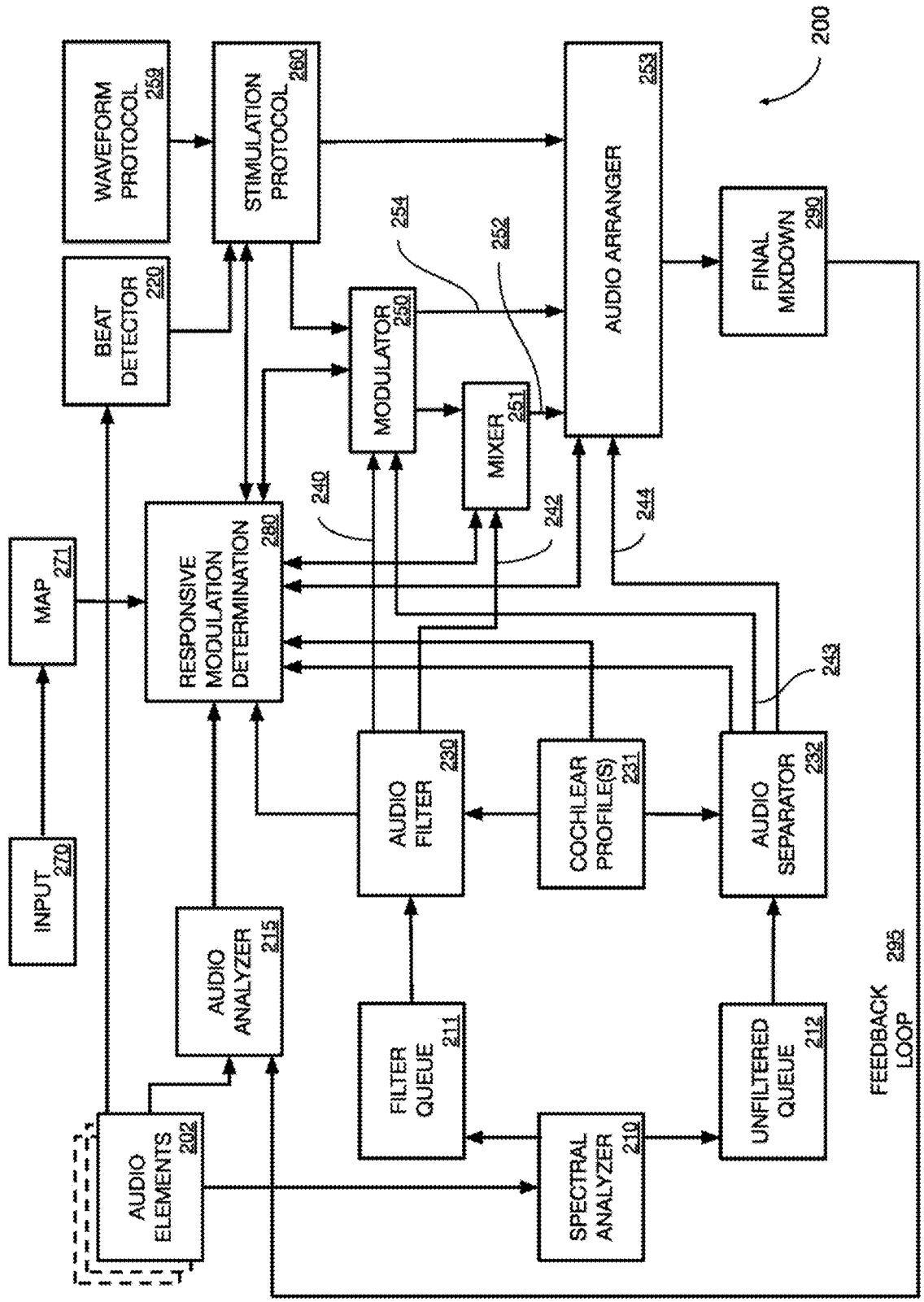
FIG. 2 is a process flowchart according to an example embodiment of the present disclosure.

FIG. 2 depicts an example process flowchart 200 to combine a modulation characteristic with audio content. Elements may be added or removed from process flow 200 without deviating from the inventive concepts of the present application.

In an example embodiment, one or more audio elements 202 can be provided to spectral analyzer module 210. Spectral analyzer module 210 can analyze the frequency components of the one or more audio elements 202. Spectral analysis, as used herein, may refer to sonographic representations and mathematical analysis of sound spectra, or by mathematically generated spectra. A spectral analyzer may use one or more of methods known to those skilled in the art, which methods include parametric or non-parametric; real-time or precomputed; assumption-based (e.g., 'frequency estimation' or a priori knowledge about tones, etc.) or non-assumption based (i.e., without any a priori knowledge); time-frequency analysis (representing how the signal changes over time); or spectral analysis (without time).

Spectral range, spectral region, or sub-bands can refer to specific bands of frequencies within the spectra. As described in greater detail below, the spectral analyzer module 210 may be used to determine how the frequency components of the one or more audio elements 202 can be utilized to implement the non-invasive neural stimulation techniques of the present disclosure.

In an example embodiment, spectral analyzer module 210 analyzes the frequency components of each of the one or more audio elements 202. If it is determined that the one or more audio elements 202 are composed of a large variety of frequency components across the spectrum, the one or more audio elements 202 can be sent to the filter queue module 211, which is a queue for audio filter module 230. Because the stimulation protocol 260 may be applied to a specific frequency or a relatively narrow range of frequencies, the one or more audio elements 202 that contain a large variety of frequency components may undergo filtering in the audio filter module 230 to separate these large varieties of frequency components. For example, audio elements that contain audio from a plurality of instruments may contain audio data with frequency components that cross the audible frequency spectrum. Because the stimulation protocol 260 can only be applied to a subset of these frequencies, such audio elements are sent to audio filter module 230. In other words, the filtering of the audio filter module 230 selects a frequency range from an audio element for modulation. It will be understood by those skilled in the art, that filter queue 211 and unfiltered queue 212 are optional, and audio components may alternatively be processed with, for example, immediate or parallel filtering, or separation.

In an example embodiment, if it is determined that one or more audio elements 202 has a single frequency component, or if most of the acoustic energy of the one or more audio elements is centered around a narrow band, then the one or more audio elements 202 are sent to unfiltered queue 212. In other words, if the one or more audio elements 202 are largely constrained to a sufficiently narrow frequency range, the stimulation protocol 260 may be applied to the entire one or more audio elements 202, and therefore, no further filtering would be required. Accordingly, the one or more audio elements 202 are sent to audio separator module 232. Audio separator module 232 looks at the spectral data of the one or more audio elements and pairs it with a cochlear profile to determine if the one or more audio elements should be modulated or not.

Additionally, spectral data may be sent from spectral analyzer module 210 to one or more of audio filter module 230 and audio separator module 232. This spectral data may be used, for example, in conjunction with cochlear profile 231, to determine which portions of the one or more audio elements 202 are to be modulated according to stimulation protocol 260.

In an example embodiment, both the audio filter module 230 and audio separator module 232 can be configured to filter audio elements for modulation (in the case of the audio filter module 230) or select audio elements for modulation (in the case of selector 232) based upon one or more cochlear profiles 231. Cochlear profile 231 may provide instructions to the audio filter module 230 and/or audio separator module 232 based upon frequency ranges that correspond to regions of the cochlea of the human ear. According to an example embodiment, cochlear profile refers to a list of frequency bands to be modulated. Frequencies not included in the list of frequency bands of the cochlear profile can be excluded from modulation. The cochlear profile may apply to many users or be derived from measurements of an individual's hearing.

The frequency data obtained by filtering the one or more audio elements in the audio filter module 230 can be (i) sent to modulator 250 for modulation according to stimulation protocol 260 (line 240), or (ii) sent to mixer 251 without modulation (line 242) for recombination with the modulated components for inclusion in a final audio element.

In an example embodiment, audio filter module 230 may receive instructions from the cochlear profile 231 for each audio element being filtered. These instructions may indicate which frequency range within the one or more audio elements 202 are to be modulated; for example, the frequencies corresponding to the less sensitive portions of the human cochlea. In carrying out this operation, audio filter module 230 may use one or more bandpass filters (or high/low-pass filters) to extract the chosen frequency components for modulation 240. According to example embodiments, band stop filters, equalizers, or other audio processing elements known to those skilled in the art may be used in conjunction with or as an alternative to the band pass filter to separate the contents of filter queue module 211 into frequency components for modulation 240 and frequency components that will not receive modulation 242.

The audio content for modulation 240, 243 can be passed to modulator 250 after being filtered by audio filter 230 or separated out by audio separator 232 in accordance with cochlear profiles 231. The remainder of the frequency components 242, 244 can be passed directly (i.e., unmodulated) to the mixer 251 where modulated and unmodulated frequency components can be recombined to form a combined audio element 252. Similarly, modulated elements 254 and unmodulated elements 244, 242 (via the mixer as shown in 252) can be passed separately into the audio arranger 253 which also acts as a mixer of concurrent audio. Audio arranger 253, described in detail subsequently, can directly receive the one or more audio elements that the system declined to filter or modulate. This process from the spectral analyzer 210 through to the audio arranger 253 (where elements are recombined) can be done for each of the one or more audio elements in the filter and unfiltered queue modules (211 and 212, respectively).

Similarly, audio separator module 232 may receive instructions from the cochlear profile 231 selected for each of the one or more audio elements. Based upon the instructions provided by cochlear profile 231, audio separator module 232 may separate the audio elements contained in unfiltered queue 212 into audio elements to be modulated (line 243) and audio elements not to be modulated (line 244). Accordingly, audio output from the audio separator 232 can be (i) sent to modulator 250 (line 243); or (ii) sent to the audio arranger 253 without modulation (line 244) for recombination and inclusion in the final audio output.

In an example embodiment, modulator 250 may apply stimulation protocol 260 to the frequency components for modulation 240 and the audio elements to be modulated 243. The stimulation protocol 260 may specify the duration of the auditory stimulation, as well as the desired stimulation across that timeframe. To control the stimulation, the stimulation protocol 260 may continually instruct the modulator 250 as to the rate, depth, waveform, and phase of the modulations.

In an example embodiment, to ensure that the stimulation protocol 260 aligns with the rhythmic elements of the audio elements being modulated, the phases of the stimulation modulation and the rhythmic elements of the audio element may be aligned. For example, applying 2 Hz modulation to a 120 BPM MP3 file may not align with the rhythmic elements of the MP3 file if the phase of the stimulation modulation is not aligned with the MP3 file. For example, if the maxima of the stimulation modulation is not aligned with the drum beats in the MP3 file, the drum beats would interfere with the stimulation modulation, and the stimulation protocol may cause audio distortion even through the stimulation modulation is being applied with a frequency that matches the rate of a 2 BPM audio element.

Such distortion may be introduced because, for example, MP3 encoding may add silence to the beginning of the encoded audio file. Accordingly, the encoded music would start later than the beginning of the audio file. If the encoded music begins 250 milliseconds after the beginning of the encoded MP3 file, stimulation modulation that is applied at 2 Hz starting at the very beginning of the MP3 file can be 180° out of phase with the rhythmic components of the MP3 file. To synchronize the modulations to the beats in the file, the phase of the modulation can be shifted by 180°. If the phase of the modulation is adjusted by 180°, the modulation cycle can synchronize with the first beat of the encoded music.

In an example embodiment, to ensure that the stimulation modulation aligns with the rhythmic elements of the audio elements being modulated, the audio elements can be provided to a beat detector, an example of which is illustrated as beat detector module 220 of FIG. 2. Beat detection can be a process of analyzing audio to determine the presence of rhythms and their parameters, such that one can align the rhythms of one piece of audio with the rhythms of another. Accordingly, beat detector module 220 may detect rhythms in music or rhythmic auditory events in non-music audio. Beat detector module 220 may detect the phase (peak and trough locations) and rate of the rhythms. Rhythmic information may already be known about the one or more audio elements 202 through, for example, metadata included in (or associated with) the one or more audio elements 202. This rhythmic information may indicate the phase where the rhythm of the audio element begins (e.g., at a particular phase) or that the rhythmic element has a defined rhythm rate (e.g., defined in BPM of the audio element). Beat detector module 220 may be configured to read or interpret this data included in the one or more audio elements 202. Beat detector module 220 can define an audio element by a single tempo but may also track a changing beat over time.

According to example embodiments, the beat detector module 220 may be configured to analyze the content of the one or more audio elements to determine information such as the phase and BPM of audio elements 202. For example, according to an example, five musical pieces can be selected, and each musical piece can be represented as a WAV file, six minutes long. Beat detector module 220 may determine that each of the musical pieces has a BPM of 120. Beat detector module 220 may further determine that each musical piece starts immediately, and therefore, each musical piece has a starting phase of 0. According to other examples, beat detector module 220 may determine that each musical piece has a silent portion prior to the start of the musical piece, such as the 250-millisecond delay provided by some MP3 encoding. Beat detector module 220 may detect this delay and convert the time delay into a phase shift of the rhythmic elements of the music based upon the BPM of the musical piece. As illustrated in FIG. 2, the data determined by beat detector module 220 is provided to stimulation protocol 260. This data may be used to ensure that the modulation provided by the stimulation protocol aligns with the rhythmic elements of the audio elements being modulated.

In an example embodiment, stimulation protocol 260 can be based upon data provided by the beat detector module 220, and waveform protocol 259. Waveform protocol 259 can define the modulating waveshape and may be used to shape neural activity more precisely within each cycle, rather than just setting the rate (cycles per second). The waveform shape may be used to target specific patterns of brain activity or specific brain regions by specifying the waveform of the modulation pattern applied to the audio elements being modulated. Entrainment to sound by the brain may vary in strength, extent, and consequence, depending on the shape of the modulation driving the entrainment. Sine waveform modulation may be used if stimulation is intended to target a single frequency of neural oscillations, and more complex waveforms may be used to drive multiple frequencies of neural oscillations.

In an example embodiment, waveform protocol 259 may be configured to provide waveforms that target specific patterns of activity or areas of the brain. Since the waveform is shaped using the presently disclosed techniques, more complex activity patterns can be targeted or activity in specific regions of the brain can be altered. Neural oscillatory waveforms may differ dramatically depending on the region of the brain being measured; different regions of the brain exhibit different waveform shapes in their neural oscillations. Even if two brain regions are firing at the exact same rate, the purpose of the oscillation may be different, and the different purpose may be expressed through different waveforms. Matching the waveform of the stimulation to the brain region being targeted may enhance the effectiveness of neural stimulation and may enhance the targeting of specific brain regions. Similarly, the waveform shape can be tuned to elicit activity patterns (measured at one point or many across the brain) different from those elicited by a sine-modulated waveform at the same rate.

In an example embodiment, once a stimulation protocol 260 has been generated, the protocol that may take into account the output of one or more of beat detector module 202 and waveform protocol 259. The stimulation protocol 260 can be provided to modulator 250. The stimulation protocol 260 may specify the duration of the auditory stimulation, as well as the desired stimulation across that timeframe. To control the stimulation, the stimulation protocol 260 may continually instruct the modulator 250 as to the rate, depth, waveform and phase of the modulations. As described previously, the stimulation protocol 260 may instruct the modulator 250 based upon the output of beat detector module 220 to ensure the rates are multiples or factors of the BPM measured by rhythmic content in the audio elements 202. A modulation waveform may be specified in the waveform protocol 259 and used to effect neural oscillatory overtones and/or to target specific brain regions, which can be provided to the modulator 250 via stimulation protocol 260. Finally, modulation phase control of the modulator 250 may be provided by stimulation protocol 260 based upon the beat detector module 220 ensuring the phase of modulation matches the phase of rhythmic content in the one or more audio elements 202. Modulation depth control can be used to manipulate the intensity of the stimulation.

In an example embodiment, a response modulation determination module (RMD) 280 may determine what parameters to pass to various elements in the audio processing chain which may include a modulator 250, mixer 251, audio arranger 253, stimulation protocol 260, or other audio processing modules. The RMD 280 may control these parameters in a smooth coordinated manner, given input 270 transformed by mapping function 271 into a single-dimensional desired modulation characteristic (e.g., low-to-high modulation depth at a particular rate) which can vary over time. The goal of the RMD 280 is that the audio output after the final mixdown achieves the desired modulation characteristic over the range required by the input 270 via the map 271, as previously discussed with respect to block 160. The RMD 280 may calculate how to achieve this given the processed audio elements (or knowledge of these elements sufficient to estimate a solution), which are analogous to arrows 240-244 which go to the modulator, mixer, and arranger, but are also provided to the RMD to calculate the required path 380 of FIG. 3. Instead of exact copies of audio as passed by 240-244, summary information such as sub-band envelopes, or subsamples, may be passed instead.

The RMD 280 can have knowledge of and control over possible parameterizations of the stimulation protocol 260, modulator 250, mixer 251, and/or audio arranger 253 (together these parameters represent a high-dimensional input space to the RMD 280). The RMD 280 may define a path through the input space that results in a smooth increase in the output (the value of a particular modulation characteristic at the final mixdown), for example, by sampling two or more points in the input-output space and inferring the input points between them via interpolation or the like. Once the path through input space is defined by the RMD 280, its role is simply to transfer the values from the input 270 and map 271 to the modulator 250, mixer 251, and/or audio arranger 253. Those skilled in the art will see that there are alternate ways in which RMD 280 may optimize parameters using, for example, linear regression, machine learning, or a map.

The RMD 280 may find this optimal path under various constraints, which may be implemented as cost functions by a constraints checker (subsequently described with respect to FIG. 3). These may include reducing overall dissimilarity (other than modulation) between pre- and post-processed audio, having all audio elements contribute to the final mixdown in some form, reducing impact on other aspects of the music's beat patterns, preserving relationships between groups of audio elements, and other constraints which may affect the aesthetic or neural-effective value of the output, up to predefined tolerance levels. In an example embodiment, a constraints checker may impose a cost function on various aspects of the analyzed output from audio analyzer 215, which can be taken into consideration by the receiving module (maximum-finder or path-creator) in deciding whether an input-output pair is acceptable in the final path.

Constraints can be used to impose alternative goals for the output audio. For example, adding a cost for brightness (high-frequency energy which may be undesirable to the listener), may find parameter solutions that balance the desired modulation characteristic against that constraint, for example by mixing down a cymbal track even though it adds to modulation depth (thus reducing the maximum possible modulation depth for the song). The cochlear profile 231 used to separate and filter audio elements with respect to their frequency ranges can also be used by the RMD 280 as a constraint in this way, for example by penalizing output mixes with too much energy in particular frequency ranges. Thus, those skilled in the art will recognize that the RMD 280 as described may be useful not only for the responsive determination of modulation but also for any other characteristic or features of audio, for example, brightness.

Figure 3:
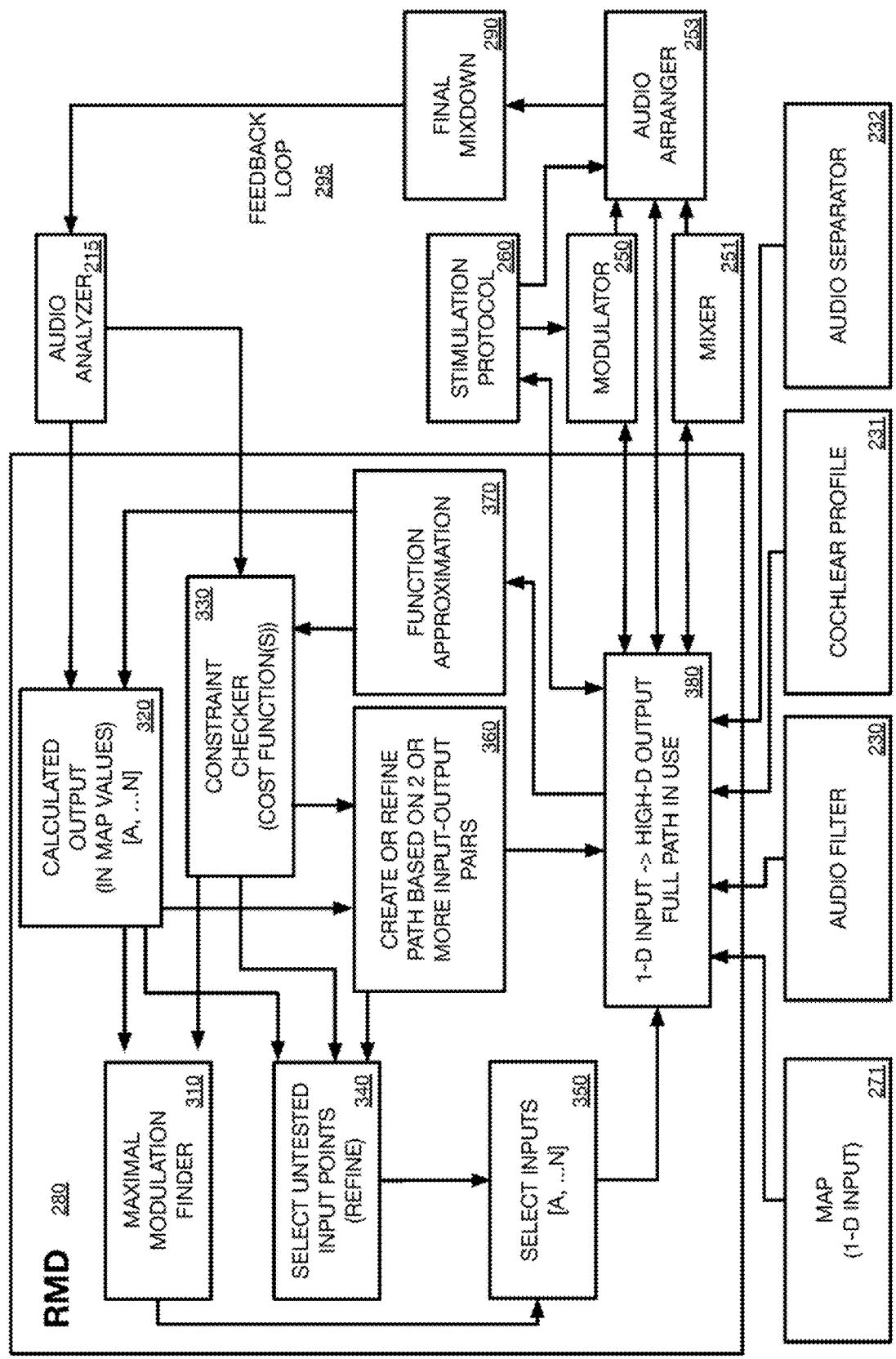
FIG. 3 is a process flowchart according to an example embodiment of the present disclosure.

FIG. 3 depicts an example process flowchart illustrating the interaction between the RMD 280 and the map 271, audio analyzer module 215, modulator 250, mixer 251, audio arranger 253, audio filter 230, cochlear profile 231, audio separator 232, and stimulation protocol 260. In various example embodiments, the RMD 280 may sample the input-output space by making use of the full processing chain with a feedback loop 295. The RMD 280 can contain a separate system to do similar computations. For example, samples of the audio element of at least 100 ms (capturing a 10 Hz cycle) or longer may be used. Alternatively, samples of up to 1 s (1000 ms) may be sufficient to achieve a good estimate of modulation characteristics.

In an example embodiment, analytic methods (function approximation 370) may be used to solve for the whole input-output space, instead of using the full processing chain to sample the space point-by-point. For example, since sound combines linearly and the modulating waveshapes are slow relative to the underlying audio signal, it can be efficient to model how the audio combines just at the modulated peaks and troughs, ignoring the majority of the modulating cycle and underlying audio. Alternatively, operating on subsamples of the audio signal can be an efficient way to estimate the input-output relationships that would result from the full processing chain. This may give the full input-output space at some resolution and the global maximum output could be selected (and corresponding inputs known). Analytic methods like this can be used to set the initial input to the RMD 280, or in lieu of the processing chain entirely (to establish the RMD 280 path without full audio processing or simulation).

The role of the RMD 280 can be to find a path of two or more points through the high-dimensional space of inputs to modulator 250 and/or mixer 251, that results in a smooth change in the desired modulation characteristics (depth, rate, spectrum, etc.) after the final mixdown 290, while satisfying constraints like reducing changes to the original audio outside of its modulation characteristics. This path (high-D to 1-D map) can be established by first establishing a putative maximum and minimum for the path, then interpolating between these points in input space (and/or extrapolating if needed). This path can also be defined by other means like sampling a large number of input space points or can be guided by human input for its initialization.

In an example embodiment, the RMD 280 may start by asking what is the heaviest amount of modulation that can be delivered under the constraints specified, which will include aesthetic constraints. This is a putative maximum output value, and maps to a specific point on the input space. Finding this value can be the role of the maximal modulation finder 310. This can be done by any number of optimization methods such as coordinate or gradient descent, branch-and-bound methods, or others. Heuristic methods can also be used that include knowledge of the problem space, such as special rules (e.g., 'never turn down the bassiest element'). The maximal modulation finder can use knowledge of aesthetic tolerances (what sort of signal is unacceptable for the listener) which can come from models of psychophysical data or by testing listeners directly. The maximal modulation finder 310 may finally accept an input vector (i.e., a point in high-dimensional space) that produces the highest output modulation value balanced against constraints which might be imposed as a cost function on other features measured by audio analyzer 215 such as roughness, distortion, difference from original, or other constraints. This input is taken as point A and passed to the path-creator as a putative maximum, along with other input-output points, likely including a putative minimum.

In some embodiments, the putative minimum modulation level may in a simple case be defined as 'no added modulation' (input vector at [0, . . . , 0]), or the minimum level might be defined by a point in the input space where the output modulation characteristic (e.g., energy at a particular modulation rate) is yet lower than the unprocessed case. For example, this could involve up-mixing audio elements with rates other than the target, such that the overall modulation spectrum has a dip at the target, and this input setting (controlling the mixer) is defined as the RMD minimum. Such a global minimum can be found with a similar constrained optimization process to that used to find the global maximum.

In an example embodiment, these putative max and min modulation levels defined by the RMD 280 may be defined as corresponding to the max and min values in the range of values taken by map 271, or as some subsection or supersection along that dimension. Then, output 'final mixdowns' with input-map values between these extremes can be obtained by setting the inputs to midway along the line connecting them in input space (interpolation). This can be a role of the path-creation module 360. More broadly the path-creation module may take two or more points in a high-dimensional input space (that have been accepted or refined as good input points to have along the path) and creates a one-dimensional path through the high-dimensional space via interpolation, extrapolation, or any other inference process. This may allow one-dimensional control of the high-dimensional inputs, which can then be smoothly varied over this range.

In some cases, a simple linear interpolation through the input space may not produce a smoothly-changing output modulation level, and so points along and nearby the interpolated line can be sampled to determine the smoothness of the output (measured modulation characteristics) after final mixdown, and the input-output path can be warped accordingly by the RMD 280 (this is depicted inside the RMD 280 in the 'Refine' loop 340). This process of optimization along the path can involve finding best solutions through machine learning methods including gradient descent.

In an example embodiment, the RMD 280 may require knowledge of the stimulation protocol (the applied modulation), but there are aspects of the stimulation protocol that may be superseded by the RMD 280, since the input 270 (e.g., from sensors) may be used to dictate modulation characteristics usually imposed by the stimulation protocol, such as modulation depth or rate. In a sense the RMD 280 functions partly as an automatic responsive stimulation protocol module (in that it changes modulation characteristics over time). The RMD 280 and stimulation protocol 260 may both control the same parameter of modulator 250, for example the applied modulation depth. sensor-input value 270 may then be 'additional' to the underlying stimulation protocol. Or, since the stimulation protocol is part of the processing-feedback loop training the RMD 280, the RMD 280 may effectively negate the stimulation protocol and produce only the output required by map 271. In an example embodiment, the stimulation protocol 260 may be barred from controlling parameters controlled by the RMD.

In example embodiments, the input-output problem solved by the RMD 280 under constraints can be approached by any number of optimization methods (including those involving machine learning or adaptive algorithms). Two simple methods of exploring the input-output space and estimating global minima and maxima can be: Modulation determination by trial-and-error (random search), and modulation determination by an optimization algorithm.

With a trial-and-error method, the RMD 280 may for example start with the understanding that the values it gets from map 271 are exactly the values that should be passed to the modulator 250 and/or mixer 251, and/or audio arranger 253. After being processed through to the final mixdown 290, a feedback loop 295 can be used by the RMD 280 to detect that the final output is not as desired, but now it has two input-output reference points. From here, depending on these points, the system may extrapolate to infer further input-output points along that axis, or may decide to take a different direction, for example if the detriment to the original audio was too great (or some other constraint was violated). When an acceptable vector is found, extrapolation can continue up to the limit of constraints, thus defining the maximum value (heaviest modulation level to allow).

With the optimization algorithm, instead of starting with a random vector, the RMD 280 may find its single best estimate of a global maximum: what settings produce the heaviest acceptable modulation? This may be done by sampling the space widely and seeding a local search algorithm such as nearest-neighbor or gradient descent; machine learning methods can be used in aid of this optimization problem. These processes including trial-and-error method and optimization algorithm may be implemented in maximum modulation finder 310 and may use the whole processing chain to sample the space, and/or contain internal simulations or function approximations. Once a solution is found, interpolation through the input space from [0, . . . , 0] to this global maximum [X, . . . , Z] may map to the range of the modulation characteristic demanded by the sensor-input value, e.g., modulation depth 0-100%. In this case, the system may, for example, infer via linear interpolation that modulation depth of 50% is produced when the modulator and mixer inputs are set to [X/2, . . . , Z/2].

The RMD 280 may perform path-determination at various intervals, for example a single input-output path could apply for the entire duration of the original audio, essentially assuming any unsampled durations are similar to any sampled durations. Or, for example, operating in a continuous fashion and changing over time as the audio does. For recorded audio elements this might involve time-windowing and modifying the input-output function for each window. If working in real time such a system may require a buffering period of at least one modulation-window (100 ms-1 s or more) to determine how to change the inputs to the modulator 250 and/or mixer 251 to account for changes in the underlying audio elements. In a 'monitoring mode' audio analysis 215 may run through the feedback loop 295 continuously or at set intervals, and the RMD 280 may only update if there is a sufficient discrepancy between expected and observed levels of modulation (e.g., as a musical piece changes). In a resource-unlimited mode, the RMD 280 may treat each time-window separately and find the best parameters to solve for the desired output modulation in a continuous manner (second-by-second).

The modulator 250 may use a low-frequency oscillator, which contains ongoing rate, phase, depth, and waveform instruction. Low frequency oscillation (LFO) is a technique where a oscillator, that operates at a lower frequency than the signal being modulated, modulates the audio signal, thus causing a difference to be heard in the signal without the actual introduction of another audio source. An LFO is often used by electronic musicians to add vibrato or various effects to a melody. In this case it can be used to affect modulation characteristics, for example modulating the amplitude, frequency, stereo panning or filters according to the stimulation protocol 260 or control signals from the RMD 280.

The modulator 250 can be used to modulate frequency components 240 and unfiltered audio elements 243. Frequency components 240 may be modulated and then mixed with their counterpart unmodulated components 242 in mixer 251 to produce final filtered, modulated audio elements 252, which are then sent to the audio arranger 253. Audio elements 243, on the other hand, are modulated in full, so they need not be remixed, and are therefore sent directly to the audio arranger 253.

An audio arranger 253 can be a device or process that allows a user to define a number of audio components to fill an audio composition with music wherever the score has no implicit notes. Accordingly, in an example embodiment, an audio arranger 253 may arrange all audio content across the timeline of the stimulation protocol 260. As illustrated in FIG. 2, stimulation protocol 260 may send its timeframe to the audio arranger 253. In this embodiment, audio arranger 253 creates the final audio arrangement. The audio arranger 253 can be used to ensure that modulated content is always present and is always coupled with unmodulated content. Filtered, modulated audio elements 252 automatically contain modulated and unmodulated content, but the audio arranger 253 would still arrange them for maximum coverage across the timeline. Modulated audio elements 254 and unmodulated audio elements 244 may be arranged such that a modulated element is always paired with an unmodulated element, such that there are always at least two elements present throughout the timeline. Since the audio arranger 253 also mixes concurrent audio elements, it also functions as a mixer and in an example embodiment may be controlled by the RMD 280 as the modulator 250 and mixer 251 are, since its parameter settings affect the final output characteristics.

The audio arranger 253 may take component elements, then replicate and distribute them over arbitrarily long timescales. Input from the user (human 'composer') might include: Density of elements in time (i.e., spacing in time), density of concurrent elements (i.e., spacing not-in-time), spatialization (e.g., panning, virtual movement), variability introduced across the elements (e.g., automated changes in key, tempo, or other musical or acoustic features), and change-over-time of the above (e.g., user-defined trajectories over input space).

According to an example embodiment, elements may be placed by evaluating their musical or acoustic features, determining whether there will be conflicts, and avoiding conflicts. Elements that are well suited for arrangement may be determined based on relationships (e.g., temporal, or spectral). For example, elements that overlap in frequency and thus mask each other or interact on the cochlea, may be disallowed to co-occur in time.

Once arrangement is complete, the arranged audio element can be sent to the final mixdown 290 which may provide a final mixdown and encodes the full audio onto an electronic medium. Final mixdown may refer to the final output of a multi-track audio arrangement. A multitrack recording has more than one individual track, or more than one piece of audio layered on top of another, to be played simultaneously. The final output of multitrack audio can also be referred to as the mixdown. The mixdown can optionally be fed back to audio analyzer 215 to form a feedback loop 295 whereby RMD 280 can iteratively approach optimal modulation characteristics.

Figure 4:
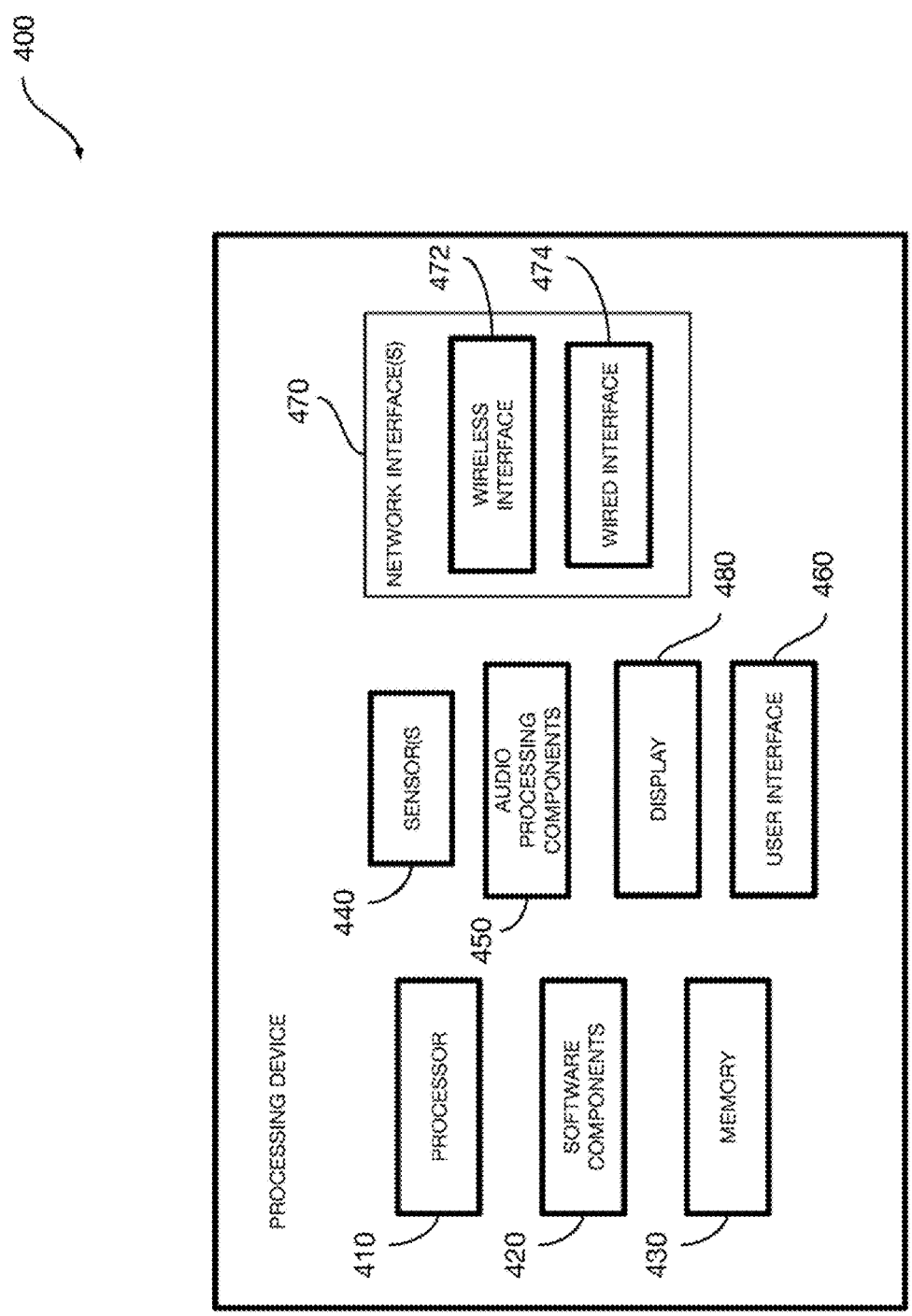
FIG. 4 is a functional block diagram of a processing device according to an example embodiment of the present disclosure.

FIG. 4 shows a functional block diagram of an example processing device 400 that can implement the previously described method 100. The processing device 400 includes one or more processors 410, software components 420, memory 430, one or more sensor inputs 440, audio processing components (e.g. audio input) 450, a user interface 460, a network interface 470 including wireless interface(s) 472 and/or wired interface(s) 474, and a display 480. The processing device may further optionally include audio amplifier(s) and speaker(s) for audio playback. In one case, the processing device 400 may not include the speaker(s), but rather a speaker interface for connecting the processing device to external speakers. In another case, the processing device 400 may include neither the speaker(s) nor the audio amplifier(s), but rather an audio interface for connecting the processing device 400 to an external audio amplifier or audio-visual playback device.

In some examples, the one or more processors 410 include one or more clock-driven computing components configured to process input data according to instructions stored in the memory 430. The memory 430 may be a tangible, non-transitory computer-readable medium configured to store instructions executable by the one or more processors 410. For instance, the memory 430 may be data storage that can be loaded with one or more of the software components 420 executable by the one or more processors 410 to achieve certain functions. In one example, the functions may involve the processing device 400 retrieving audio data from an audio source or another processing device. In another example, the functions may involve the processing device 400 sending audio data to another device or a playback device on a network.

The audio processing components 450 may include one or more digital-to-analog converters (DAC), an audio preprocessing component, an audio enhancement component or a digital signal processor (DSP), and so on. In one embodiment, one or more of the audio processing components 450 may be a subcomponent of the one or more processors 410. In one example, audio content may be processed and/or intentionally altered by the audio processing components 450 to produce audio signals. The produced audio signals may be further processed and/or provided to an amplifier for playback.

The network interface 470 may be configured to facilitate a data flow between the processing device 400 and one or more other devices on a data network, including but not limited to data to/from other processing devices, playback devices, storage devices, and the like. As such, the processing device 400 may be configured to transmit and receive audio content over the data network from one or more other devices in communication with the processing device 400, network devices within a local area network (LAN), or audio content sources over a wide area network (WAN) such as the Internet. The processing device 400 may also be configured to transmit and receive sensor input over the data network from one or more other devices in communication with the processing device 400, network devices within a LAN or over a WAN such as the Internet. The processing device 400 may also be configured to transmit and receive audio processing information such as, for example, a sensor-modulation-characteristic table over the data network from one or more other devices in communication with the processing device 400, network devices within a LAN or over a WAN such as the Internet.

As shown in FIG. 4, the network interface 470 may include wireless interface(s) 472 and wired interface(s) 474. The wireless interface(s) 472 may provide network interface functions for the processing device 400 to wirelessly communicate with other devices in accordance with a communication protocol (e.g., any wireless standard including IEEE 802.11a/b/g/n/ac, 802.15, 4% mobile communication standard, and so on). The wired interface(s) 474 may provide network interface functions for the processing device 400 to communicate over a wired connection with other devices in accordance with a communication protocol (e.g., IEEE802.3). While the network interface 470 shown in FIG. 4 includes both wireless interface(s) 472 and wired interface(s) 474, the network interface 470 may in some embodiments include only wireless interface(s) or only wired interface(s).

The processing device may include one or more sensor(s) 440. The sensors 440 may include, for example, inertial sensors (e.g., accelerometer, gyrometer, and magnetometer), a microphone, a camera, or a physiological sensor such as, for example, a sensor that measures heart rate, blood pressure, body temperature, EEG, MEG, Near infrared (fNIRS), or bodily fluid. In some example embodiments, the sensor may correspond to a measure of user activity on a device such as, for example, a smart phone, computer, tablet, or the like.

The user interface 460 and display 480 can be configured to facilitate user access and control of the processing device. Example user interface 460 include a keyboard, touchscreen on a display, navigation device (e.g., mouse), etc.

The processor 410 may be configured to receive a mapping of sensor-input values and modulation-characteristic values, wherein each sensor-input value corresponds to a respective modulation-characteristic value. This aspect is similar to block 110 of the method 100. The processor 410 may be configured to receive an audio input from an audio source (not shown), wherein the audio input comprises at least one audio element, each comprising at least one audio parameter. This aspect is similar to block 120 of the method 100.

The processor 410 may be configured to identify an audio-parameter value of the audio parameter. This aspect is similar to block 130 of the method 100. The processor 410 may be configured to receive a sensor input 440 from a sensor (not shown). This aspect is similar to block 140 of the method 100.

The processor 410 may be configured to select from the mapping of sensor-input values and modulation-characteristic values, a modulation-characteristic value that corresponds to the sensor-input value. This aspect is similar to block 150 of the method 100.

The processor 410 may be configured to generate an audio output based on the audio-parameter value and the modulation-characteristic value. This aspect is similar to block 160 of the method 100. The processor 410 may be configured to play the audio output. This aspect is similar to block 170 of the method 100.

Figure 5:
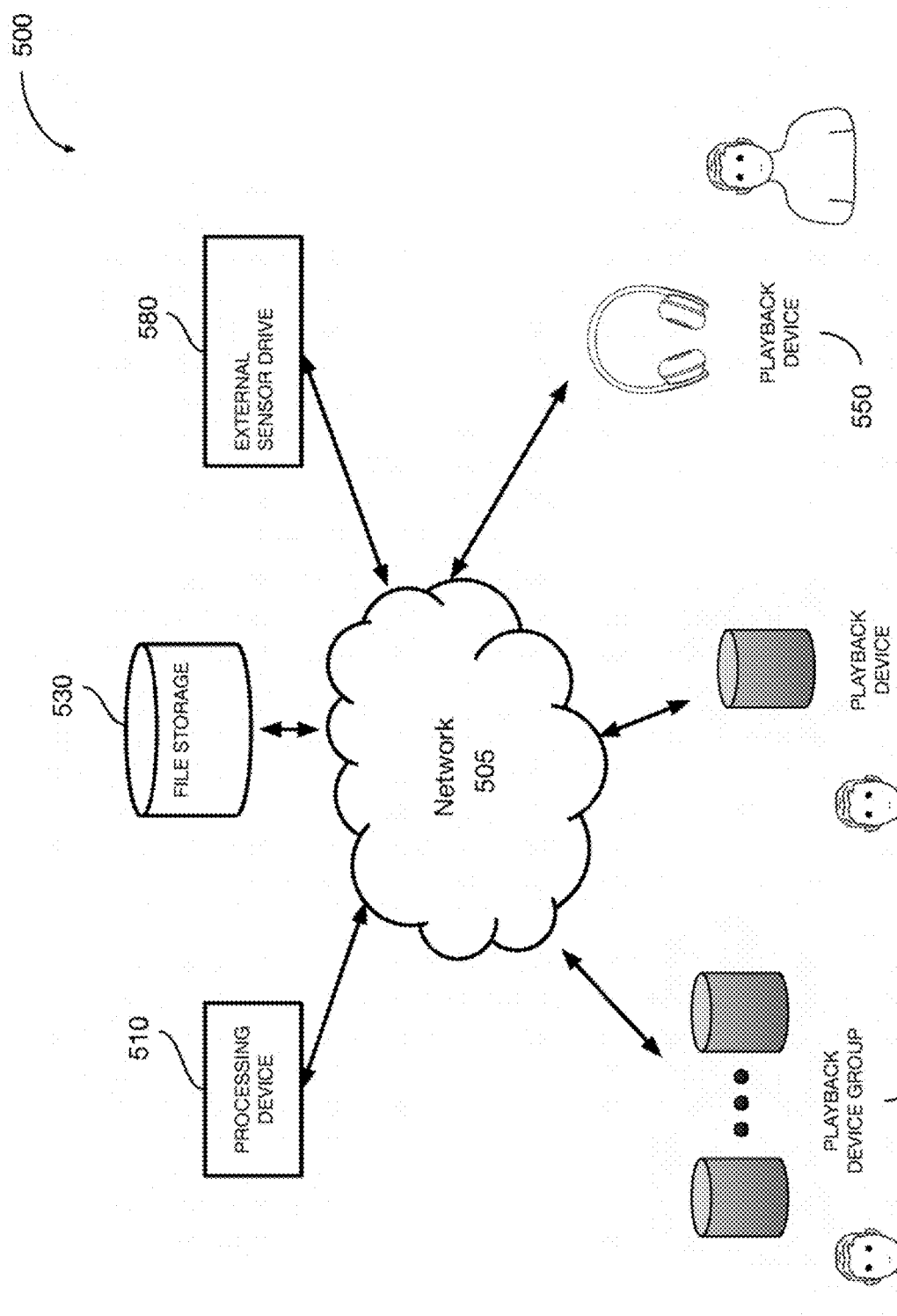
FIG. 5 is an example system with various components according to an example embodiment of the present disclosure.

Aspects of the present disclosure may exist in part or wholly in, distributed across, or duplicated across one or more physical devices. FIG. 5 illustrates one such example system 500 in which the present invention may be practiced. The system 500 illustrates several devices (e.g., computing device 510, audio processing device 520, file storage 530, playback device 550, 560, and playback device group 570) interconnected via a data network 505. Although the devices are shown individually, the devices may be combined into fewer devices, separated into additional devices, and/or removed based upon an implementation. The data network 505 may be a wired network, a wireless network, or a combination of both.

In some example embodiments, the system 500 can include an audio processing device that can perform various functions, including but not limited to audio processing. In an example embodiment, the system 500 can include a computing device 510 that can perform various functions, including but not limited to, aiding the processing by the audio processing device 520. In an example embodiment, the computing devices 510 can be implemented on a machine such as the previously described system 500.

In an example embodiment, the system 500 can include a storage 530 that is connected to various components of the system 500 via a network 505. The connection can also be wired (not shown). The storage 530 can be configured to store data/information generated or utilized by the presently described techniques. For example, the storage 530 can store the mapping of sensor-input values and modulation-characteristic values, as previously discussed with respect to the step 110. The storage 530 can also store the audio output generated in the step 170.

In an example embodiment, the system 500 can include one or more playback devices 550, 560 or a group of playback devices 570 (e.g. playback devices, speakers, mobile devices, etc.). These devices can be used to playback the audio output, as previously described in the step 180. In some example embodiments, a playback device may include some or all of the functionality of the computing device 510, the audio processing device 520, and/or the file storage 530. As described previously, a sensor can be based on the audio processing device 520 or it can be an external sensor device 580 and data from the sensor can be transferred to the audio processing device 520.

Additional examples of the presently described method and device embodiments are suggested according to the structures and techniques described herein. Other non-limiting examples may be configured to operate separately or can be combined in any permutation or combination with any one or more of the other examples provided above or throughout the present disclosure.

It will be appreciated by those skilled in the art that the present disclosure can be embodied in other specific forms without departing from the spirit or essential characteristics thereof. The presently disclosed embodiments are therefore considered in all respects to be illustrative and not restricted. The scope of the disclosure is indicated by the appended claims rather than the foregoing description and all changes that come within the meaning and range and equivalence thereof are intended to be embraced therein.

It should be noted that the terms "including" and "comprising" should be interpreted as meaning "including, but not limited to". If not already set forth explicitly in the claims, the term "a" should be interpreted as "at least one" and "the", "said", etc. should be interpreted as "the at least one", "said at least one", etc. Furthermore, it is the Applicant's intent that only claims that include the express language "means for" or "step for" be interpreted under 35 U.S.C. 112(f). Claims that do not expressly include the phrase "means for" or "step for" are not to be interpreted under 35 U.S.C. 112(f).

The invention claimed is:

1. A method comprising:
   receiving, by a processing device, a mapping of sensor-input values and acoustic modulation-characteristic values, wherein each sensor-input value in the mapping corresponds to a respective acoustic modulation-characteristic value in the mapping;
   receiving, by the processing device, an audio element from an audio source;
   identifying, by the processing device, at least one audio parameter of the audio element, wherein the at least one audio parameter comprises one or more rhythmic elements of the audio element;

receiving, by the processing device, a sensor-input value from a sensor;

determining, by the processing device, from the mapping of sensor-input values and acoustic modulation-characteristic values, a desired acoustic modulation-characteristic value that corresponds to the sensor-input value received from the sensor, wherein the desired acoustic modulation-characteristic value comprises at least one of a desired speed of cyclic change in energy, a desired phase, a desired depth, or a desired waveform shape;

modifying the audio element by adding modulation to at least a portion of the audio element based on the at least one audio parameter, wherein the modified audio element includes the desired acoustic modulation-characteristic value; and playing, by the processing device, the modified audio element.

2. The method of claim 1, wherein the audio source comprises at least one of an audio signal, digital music file, musical instrument, or environmental sounds.

3. The method of claim 1, wherein the at least one audio parameter further comprises at least one of tempo, root mean square energy, loudness, event density, temporal envelope, cepstrum, chromagram, flux that indicates change in an audio frequency spectrum over time, autocorrelation that indicates a correlation of the audio element or a feature extracted from the audio element with itself as a function of lag, amplitude modulation spectrum, spectral modulation spectrum, attack and decay, roughness, harmonicity, or sparseness of the audio element.

4. The method of claim 1, wherein the sensor comprises at least one of an accelerometer, a microphone, a camera, or a physiological sensor.

5. The method of claim 4, wherein the physiological sensor comprises one or more sensors that measure heart rate, blood pressure, body temperature, EEG, MEG, Near infrared (fNIRS), or bodily fluid.

6. The method of claim 4, wherein the receiving of the sensor-input value from the sensor comprises receiving background noise from the microphone.

7. The method of claim 1, comprising:
generating the mapping of sensor-input values and acoustic modulation-characteristic values based on a type of sensor and/or an acoustic modulation characteristic.

8. The method of claim 7, comprising:
storing the mapping of sensor-input values and acoustic modulation-characteristic values in a data table.

9. The method of claim 1, further comprising:
transmitting the modified audio element to an external device.

10. The method of claim 1, wherein modifying the audio element by adding modulation to the at least a portion of the audio element based on the at least one audio parameter comprises:
adding modulation to the at least a portion of the audio element that both (i) matches at least one aspect of the desired acoustic modulation-characteristic value and (ii) aligns with the one or more rhythmic elements of the audio element.

11. A computing device comprising a processor and associated tangible, non-transitory computer-readable memory storing program instructions, wherein the program instructions, when executed by the processor, configure the computing device to perform functions comprising:
receiving a mapping of sensor-input values and acoustic modulation-characteristic values, wherein each sensor-input value in the mapping corresponds to a respective acoustic modulation-characteristic value in the mapping;

receiving an audio element from an audio source;

identifying at least one audio parameter of the audio element, wherein the at least one audio parameter comprises one or more rhythmic elements of the audio element;

receiving a sensor-input value from a sensor;

determining from the mapping of sensor-input values and acoustic modulation-characteristic values, a desired acoustic modulation-characteristic value that corresponds to the sensor-input value received from the sensor, wherein the desired acoustic modulation-characteristic value comprises at least one of a desired speed of cyclic change in energy, a desired phase, a desired depth, or a desired waveform shape;

modifying the audio element by adding modulation to at least a portion of the audio element based on the at least one audio parameter, wherein the modified audio element includes the desired acoustic modulation-characteristic value; and playing the modified audio element.

12. The computing device of claim 11, wherein the audio source comprises at least one of an audio signal, digital music file, musical instrument, or environmental sounds.

13. The computing device of claim 11, wherein the at least one audio parameter further comprises at least one of tempo, root mean square energy, loudness, event density, temporal envelope, cepstrum, chromagram, flux that indicates change in an audio frequency spectrum over time, autocorrelation that indicates a correlation of the audio element or a feature extracted from the audio element with itself as a function of lag, amplitude modulation spectrum, spectral modulation spectrum, attack and decay, roughness, harmonicity, or sparseness of the audio element.

14. The computing device of claim 11, wherein the sensor comprises at least one of an accelerometer, a microphone, a camera, or a physiological sensor.

15. The computing device of claim 14, wherein the physiological sensor comprises one or more sensors that measure heart rate, blood pressure, body temperature, EEG, MEG, Near infrared (fNIRS), or bodily fluid.

16. The computing device of claim 11, wherein the functions further comprise:
generating the mapping of sensor-input values and acoustic modulation-characteristic values based on a type of sensor and/or an acoustic modulation characteristic.

17. The computing device of claim 16, wherein the functions further comprise:
storing the mapping of sensor-input values and acoustic modulation-characteristic values in a data table.

18. The computing device of claim 11, wherein the functions further comprise:
transmitting the modified audio element to an external device.

19. The computing device of claim 11, wherein modifying the audio element by adding modulation to the at least a portion of the audio element based on the at least one audio parameter comprises:
adding modulation to the at least a portion of the audio element that both (i) matches at least one aspect of the desired acoustic modulation-characteristic value and (ii) aligns with the one or more rhythmic elements of the audio element.

20. A tangible, non-transitory computer readable medium for storing instructions which when executed by one or more processors cause a processing device to:
- receive a mapping of sensor-input values and acoustic modulation-characteristic values, wherein each sensor-input value in the mapping corresponds to a respective acoustic modulation-characteristic value in the mapping;
- receive an audio element from an audio source;
- identify at least one audio parameter of the audio element, wherein the at least one audio parameter comprises one or more rhythmic elements of the audio element;
- receive a sensor-input value from a sensor;
- determine from the mapping of sensor-input values and acoustic modulation-characteristic values, a desired acoustic modulation-characteristic value of an audio output that corresponds to the sensor-input value received from the sensor, wherein the desired acoustic modulation-characteristic value comprises a desired speed of cyclic change in energy, a desired phase, a desired depth, or a desired waveform shape;
- modify the audio element by adding modulation to at least a portion of the audio element based on the at least one audio parameter, wherein the modified audio element includes the desired acoustic modulation-characteristic value; and
- play the modified audio element.

* * * * *